United States Patent [19]
Orth

[11] Patent Number: 5,423,323
[45] Date of Patent: Jun. 13, 1995

[54] SYSTEM FOR CALCULATING COMPLIANCE AND CARDIAC HEMODYNAMIC PARAMETERS

[75] Inventor: Jeffrey L. Orth, Salt Lake City, Utah

[73] Assignee: Rocky Mountain Research, Inc., Salt Lake City, Utah

[21] Appl. No.: 114,314

[22] Filed: Aug. 30, 1993

[51] Int. Cl.$^6$ ............................................. A61B 5/0215
[52] U.S. Cl. ..................................... 128/673; 128/668; 128/692
[58] Field of Search ................ 128/673, 675, 691–694, 128/713, 736, 748, 668

[56] References Cited

U.S. PATENT DOCUMENTS

| | | |
|---|---|---|
| 3,556,082 | 1/1971 | McCullough. |
| 3,920,004 | 11/1975 | Nakayama. |
| 4,227,407 | 10/1980 | Drost. |
| 4,357,106 | 11/1982 | Tschirren et al.. |
| 4,507,974 | 4/1985 | Yelderman. |
| 4,509,526 | 4/1985 | Barnes et al.. |
| 4,562,843 | 1/1986 | Djordjevich et al. .......... 128/913 X |
| 4,621,646 | 11/1986 | Bryant ................................ 128/692 |
| 4,660,564 | 4/1987 | Benthin et al.. |
| 4,669,485 | 6/1987 | Russell. |
| 4,685,470 | 8/1987 | Sekii et al.. |
| 4,691,709 | 9/1987 | Cohen. |
| 4,796,634 | 1/1989 | Huntsman et al.. |
| 4,819,655 | 4/1989 | Webler. |
| 4,836,214 | 6/1989 | Sramek. |
| 4,841,974 | 6/1989 | Gumbrecht et al.. |
| 4,841,981 | 6/1989 | Tanabe et al.. |
| 4,873,989 | 10/1989 | Einzig ................................ 128/692 |
| 4,877,035 | 10/1989 | Bogen et al. ..................... 128/692 X |
| 4,878,898 | 11/1989 | Griffin et al. ................... 128/675 X |
| 4,909,259 | 3/1990 | Tehrani. |
| 4,947,852 | 8/1990 | Nassi et al.. |
| 4,949,724 | 8/1990 | Mahutte et al.. |
| 4,953,556 | 9/1990 | Evans. |
| 4,957,115 | 9/1990 | Selker. |
| 4,979,514 | 12/1990 | Sekii et al.. |
| 5,052,395 | 10/1991 | Burton et al.. |
| 5,176,144 | 1/1993 | Yoshikoshi et al.. |
| 5,275,169 | 1/1994 | Afromowitz et al.. |

OTHER PUBLICATIONS

R. A. Wolthius; M. A. Afromowitz; G. L. Mitchell; D. Frank; T. Lenihan and M. Bouchard "A New Method for Measuring Intra-arterial Size and Arterial Wall Compliance"–FASEB J vol. 8, No. 5 (part 2); A866, 1994.

Bazett, HC.; Cotton, FS.; Laplace, LB.; & Scott, JC: "The Calculation of Cardiac Output and Effective Peripheral Resistance From Blood Pressure Measurements ... ," Am. J. Physiol., 113:312–334 (1935).

Bourgeois, MJ; Gilbert, BK; Donald, DE; Wood, EH: "Characteristics of Aortic Diastolic Pressure With Application to the Continuous Monitoring of Changes ... ," Circulation Research 35:56–66 (1974).

Dollar, ML: "Evaluation of a Continuous Thermodilution Cardiac Output Catheter," ASAIO J. 38:M351–356 (1992).

(List continued on next page.)

*Primary Examiner*—Angela D. Sykes
*Attorney, Agent, or Firm*—Trask, Britt & Rossa

[57] ABSTRACT

A catheter set (10) is used in connection with a blood flow monitor and calibration system (80) to determine the compliance C of a vessel according to the equation $C = dV2/(PE-PA)$, where dV2 is the change in volume of the vessel created by the change in volume (e.g., deflation) of a displacement balloon (30) adjacent to a catheter (14), PE is an estimate of what the pressure measured by a pressure transducer (56) or a strain gage (78) would have been but for the change in volume of the displacement balloon at a particular time, and PA is the actual pressure measured by the transducer at the particular time. The determined compliance is more accurate than that obtained through thermal dilution procedures. The determined value of compliance C may then be used in calculation of blood flow. In addition, pulmonary vascular resistance and systemic vascular resistance may calculated through procedures and in equations using the determined compliance without directly measuring the pulmonary capillary wedge pressure.

26 Claims, 5 Drawing Sheets

U.S. PATENT DOCUMENTS

Fry, DL; Mallos, AJ; & Caspe, AGT: "A Catheter Tip Method for Measurement of Instantaneous Aortic Velocity," Circulation Research, IV:627–632 (Sep. 1956).

Ganz, W.; Swan, HJC: "Measurement of Blood Flow by Thermoldilution" AM. J. Cardiology, 29:241–246 (Feb. 1972).

Greenfield, JC; & Fry, DL: "A Critique: Relationship of the Time Derivative of Pressure to Blood Flow" J. Appl. Physicl. 20(6): 1141–1147 (1965).

Guarini, M; Urzua, J; Cipriano, A; & Matus, M: "Non-linear Cardiovascular Parameter Estimation Using the Arterial Pressure Waveform," Trans of the Soc for Comp Sim (1992).

Guyton, A. et al, Circulatory Physiology: Cardiac Output and its Regulation, Chapter 5, pp. 99–107 (2nd Ed. 1973).

Hamilton, WF; & Remington, JW: "The Measurement of Stroke Volume From the Pressure Pulse" Amer. J. Physiol. 148: 14–24 (1947).

Jones, WB; Hefner, LL; Bancroft, WH; & Klip, W: "Velocity of Blood Flow and Stroke Volume Obtained from the Pulse Pressure", J. Clin Invest., 38:2087–2090 (1959).

Jones, WB; & Griffin, JB: "Comparison of Computed Aortic Blood Velocity with that of Electromagnetic Flowmeter" J. Appl. Physiol. 17(3): 482–486 (1962).

Khalil, HH: "Measurement of Cardiac Output by Thermal Dilution and Direct Fick Methods in Dogs" J. Appl. Physiol., 21: 1131–1135 (1966).

Kouchoukos, NU; Sheppard, LC; & McDonald, DA: "Estimation of the Stroke Volume in the Dog by a Pulse Contour Method," Circulation Research, 26: 611–623 (May 1970).

Kouchoukos, NT; Sheppard, LC; McDonald, DA; and Kirklin, JW: "Estimation of the Stroke Volume From the Central Arterial Pressure Contour in ... ", Surgical Forum (Cardiac Surgery) 20: 180–182 (1969).

Martin, JF; & Volfson, LB: "Determination of Continuous Cardiac Output From the Arterial Pressure Waveform: Application of Pattern Recognition and Image Processing" IEEE, 0-7803-1377–Jan. 1993, 663–664.

McDonald, DA: "The Relation of Pulsatile Pressure to Flow in Arteries" J. Physiol. 127: 533–552 (1955).

Peters, JL: "Consequences of the Diaphragm Driven Artificial Heart–Animal Implantation and Mock Circulation Studies" Chest, 63:589–597 (No. 4, Apr. 1973).

Pieper, HP: "Work of the Heart Under the Effect of Induced Arterial Pressure Oscillations Studied in Intact Anesthetized Dogs" Circulation Research, 10:285–294 (Mar. 1962).

Promotional Materials, "Portable Heart Function Monitor" Research and Development Center for Biomedical Instruments of the Beijing Polytechnic University.

Promotional Materials, "Arterial/Venous Blood Flow Measurement Methods: Comparison of Features," Transonics Systems, Ithica, NY, updated Mar. 1990.

Remington, JW; Hamilton, WF; & Dow, P: "Some Difficulties involved in the Prediction of the Stroke Volume From the Pulse Wave Velocity" Pat. J. Physiol. 536–545 (1945).

Starmer, CF; McHale, PA; Cobb, FR; & Greenfield, JC: "Evaluation of Several Methods for Computing Stroke Volume from Central Aortic Pressure" Circulation Research, 33:139–148 (Aug. 1973).

Verdouw, PD; Beaune, GQ Roelandt, J; & Hugenholtz, PG: "Stroke Volume From Central Aortic Pressure!A Critical Assessment of the Various Formulae as to Their ... " Basic Res. Cardiol. 70:377–389 (1975).

Warner, HR; Swan, HJC; Connolly, DC; Tompkins, RG; & Wood, EH: "Quantitation of Beat-to-Beat Changes the Stroke Volume From the Aortic Pulse Contour in Man" J. Appl. Physiol, 5:495–507 (Mar. 1953).

Warner, HR; Gardner, RE; & Toronto, AF: "Computer-based Monitoring of Cardiovascular Functions in Postoperative Patients" Suppl II to Circulation, vols. 37 and 38; 37:II68–II74 (Apr. 1968).

Watt, TB; & Burrus, CS: "Arterial Pressure Contour Analysis for Estimating Human Vascular Properties" J. Appl. Physiol. 40:171–176 (No. 2, Feb. 1976).

Wetterer, E: "Flow and Pressure in the Arterial System, Their Hemodynamic Relationship, and the Principles of Their Measurement" Minn,. Med. 37:77–86 (Feb. 1954).

"The Swan-Ganz Flow-Directed Thermodilution Catheter" brochure by Edwards Laboratories, 1974.

SYSTEM FOR CALCULATING COMPLIANCE AND CARDIAC HEMODYNAMIC PARAMETERS

BACKGROUND OF THE INVENTION

1. Field

The present invention relates to methods and systems for determining vessel compliance and using the determined compliance to calculate blood flow. The invention also includes methods and systems for calculating pulmonary vascular resistance and systemic vascular resistance from pressure versus time measurements for a particular compliance, without directly measuring the pulmonary capillary wedge pressure.

2. State of the Art

Cardiac output, which is the rate of flow (in liters per minute) of blood from the heart, is one measure of cardiac hemodynamics. Various procedures have been developed to determine cardiac output. The standard procedure for measuring cardiac output involves using a thermal dilution catheter, such as a Swan-Ganz flow-directed thermal dilution catheter.

In a common procedure, a thermal dilution catheter, such as a Swan-Ganz catheter, is inserted into a jugular vein in the neck. The catheter is connected to tubes through which air and liquids may be injected. To place the catheter, a balloon on the tip of the catheter is inflated. The blood flow to the heart pulls the catheter through the right ventricle into the pulmonary artery. A thermistor near the tip of the catheter is used in measuring the temperature of the blood. To determine the cardiac output, the clinician injects about 3 cubic centimeters (cc) of ice cold saline through one of the tubes to an opening some distance from the tip of the catheter. The saline mixes with and cools the blood in the right atrium of the heart. As the heart pumps, the cooled blood and saline eventually are pumped past the thermistor. The temperature of the thermistor is measured and a temperature versus time profile is generated from which the cardiac output may be calculated by a well known technique, such as the classical Stewart Hamilton equation modified for use with a thermal indicator. More specifically, the area under the temperature versus time curve is proportional to the cardiac output.

There are several sources of error in the results of thermal dilution procedures. Sources of error include variations in the rate at which the cold saline is injected, the temperature of the saline, and the position of the catheter and thermistor within the vessel. The calculated cardiac output may be ±20% or more than the actual cardiac output. Typically, the thermal dilution procedure is employed three times and an average is made of the three calculated cardiac outputs. However, multiple applications of the procedure is unsatisfactory because the patient is subjected to multiple injections of cooled saline and the attendant risk of problems, such as infection. Also, the average of three calculated cardiac outputs is still not particularly accurate.

A more recent variation of the thermal dilution procedure is described in U.S. Pat. No. 4,507,974 ("'974 patent") to Yelderman. The system described in the '974 patent includes an intravascular heating element that heats the blood, as opposed to cooling the blood through injecting a cold saline. The temperature of the blood is measured through a thermistor. The rate at which the measured temperature changes is used in calculating cardiac output. Disadvantages of the system of the '974 patent include potential blood damage as a result of using a heating element and that the accuracy of the calculated cardiac output has error approximately the same as standard thermal dilution.

Another technique for determining cardiac output was based on the work of Homer Warner in the early 1950's, which is described in A Guyton et al., "Circulatory Physiology: Cardiac Output and its Regulation," (2nd Ed. 1973), chap. 5 (hereinafter "Guyton"). Guyton explains that the during the cardiac output (CO) may be derived from equation (1), below:

$$CO = C \times F(\overline{Pcd} - \overline{Pab})(1 + Sa/Da) \qquad (1).$$

In equation (1), C is the compliance of the vessel (called "capacitance" by Guyton). The compliance is the change in volume of a vessel (in this case the arterial tree) for each unit change in pressure. F is the heart rate. Pcd is the average pressure in the arterial tree at the end of systole. Pab is the average pressure in the arterial tree at the end of diastole. Sa is the area under the arterial pressure curve during systolic drainage (shown in FIG. 5-3 of Guyton). Da is the area under the arterial pressure curve during diastolic drainage (shown in FIG. 5-3 of Guyton).

Solving for C in equation (1) produces equation (2) below:

$$C = CO/(F(\overline{Pcd} - \overline{Pab})(1 + Sa/Da)) \qquad (2).$$

Warner assumed that the compliance of a vessel is constant. With that assumption, he reasoned that the cardiac output could be calculated repeatedly through the following procedure, which involves only one flow measurement procedure. The cardiac output (CO) was initially determined using the Fick or similar procedure. The pressures of equation (1) are measured at the same time. The compliance C is determined from the measured cardiac output and pressures. Thereafter, the cardiac output may be calculated merely by determining the heart rate and measuring the pressures of equation (1). The Warner procedure may be applied continuously without injection of an indicator. It is, therefore, much less invasive than repeated Fick or thermal dilution procedures.

A major problem with the Warner procedure is that the compliance is not constant. Compliance changes significantly as, for example, the patient takes vasoactive drugs or as the condition of the patient changes. Accordingly, the Warner procedure may inaccurately calculate the cardiac output rates over time.

A second measure of cardiac hemodynamics is pulmonary vascular resistance ("PVR"), which is the resistance to blood traveling through the lungs to be oxygenated. PVR may be calculated by equation (3), below:

$$PVR = (\overline{PAP} \times PCW)/CO \qquad (3),$$

where $\overline{PAP}$ is the mean pulmonary artery pressure, PCW is the pulmonary capillary wedge pressure, and CO is the cardiac output.

The standard technique for calculating pulmonary vascular resistance is as follows. The wedge pressure is measured by inserting a catheter with a balloon at its end into one branch of the pulmonary artery connected to a lung and inflating the balloon until the artery is completely sealed off. The pressure across the lung is then measured through a lumen at the tip of the catheter. The pulmonary artery pressure is measured through standard techniques such as through pressure transducers connected to a Swan-Ganz catheter. The cardiac output is measured through a thermal dilution catheter as described above. Disadvantages of this procedure for calculating pulmonary vascular pressure include the invasiveness of measuring wedge pressure and all of the above-recited disadvantages of the thermal dilution catheter procedure.

A third measure of cardiac hemodynamics is systemic vascular resistance ("SVR"), which is a measure of the resistance of the blood flow through the body other than the lungs. The systemic vascular resistance gives a measure of the performance of the left heart and the vascular condition of the body. SVR may be calculated by equation (4), below:

$$SVR = (\overline{AOP} \times PCW)/CO \qquad (4),$$

where $\overline{AOP}$ is mean arterial pressure, PCW is the pulmonary capillary wedge pressure, and CO is the cardiac output.

A standard technique for systemic vascular resistance is as follows. First, wedge pressure of the pulmonary system is measured. Second, the cardiac output is calculated. Third, the mean arterial pressure is measured.

SUMMARY OF THE INVENTION

The present invention relates to methods and systems for determining vessel compliance. The invention also includes methods and systems for using the determined compliance to calculate blood flow. The invention also includes methods and systems for calculating pulmonary vascular resistance and systemic vascular resistance from pressure versus time measurements for a particular compliance, without directly measuring the pulmonary capillary wedge pressure.

In one embodiment of the invention, a catheter set is used in connection with a blood flow monitor and calibration system to determine the compliance C of a vessel according to the equation $C = dV2 / (PE - PA)$, where dV2 is the change in volume of the vessel created by the change in volume (e.g., deflation) of a displacement balloon adjacent to a catheter, PE is an estimate of what the pressure measured by a pressure transducer would have been but for the change in volume of the displacement balloon at a particular time, and PA is the actual pressure measured by the transducer at the particular time. The determined compliance is more accurate than that obtained through thermal dilution procedures. The determined value of compliance C may then be used in calculation of blood flow. In addition, pulmonary vascular resistance and systemic vascular resistance may calculated through procedures and in equations using the determined compliance without directly measuring the pulmonary capillary wedge pressure.

A system for determining compliance of a vessel may include a catheter that is insertable into the vessel, a displacement balloon positioned adjacent to the catheter, a first tube having at least first and second openings, the first opening being connected to the displacement balloon, and an adjustable pressure source connected to the second opening of the tube that selectively changes the volume of the displacement balloon by a predetermined amount, thereby changing the volume of the vessel by essentially the predetermined amount. The system may further include a pressure detector that measures blood pressure in the vessel at a position near the displacement balloon, and processing circuits for monitoring the pressure detector, determining the change in blood pressure caused by the change in volume of the displacement balloon, and determining the compliance through an equation that includes the change in volume and change in blood pressure. The function of determining of the change in blood pressure caused by the change in volume of the displacement balloon performed by the processing circuits includes estimating what the blood pressure would have been at a particular time but for the change in the volume of the displacement balloon.

A change in volume could be obtained by injecting or withdrawing fluid, rather than by using a displacement balloon.

In the system for determining compliance, the pressure detector may be a miniaturized strain gage or a fiber optic pressure transducer placed adjacent to the catheter. The change in volume may be a decrease in volume of the displacement balloon. The vessel may be a pulmonary artery. The displacement balloon may also act as a floatation balloon having different levels depending on whether it is acting as a displacement balloon or a flotation balloon.

The invention includes a method and system for calculating blood flow of blood in a vessel of a subject. The method may include determining the compliance of the vessel by determining a change in pressure caused by a change in volume in the vessel, and calculating the blood flow according to an equation for calculating blood flow as a function of compliance. A system for calculating blood flow of blood in a vessel of a subject, may include a system for calculating compliance and producing a signal indicative of blood pressure. The system may also include processing circuits, such as a computer, for using the pressure signal for measuring heart rate ($\overline{F}$) of the subject, for measuring the average pressure ($\overline{Pcd}$) in the arterial tree of the subject at the end of systole, measuring the average pressure ($\overline{Pab}$) in the arterial tree of the subject at the end of diastole, generating an arterial pressure curve of the subject during systolic drainage and the arterial pressure curve of the subject during diastolic drainage; measuring the area (Sa) under the arterial pressure curve during systolic drainage, measuring the area (Da) under the arterial pressure curve during diastolic drainage, and calculating BF according to the equation $BF = C \times \overline{F} (\overline{Pcd} - \overline{Pab})(1 + Sa/Da)$.

A method for calculating pulmonary vascular resistance of a subject, without directly measuring wedge pressure, may include the steps of determine the compliance C of the pulmonary artery of the subject, measuring the pulmonary artery pressure (PAP1) of the subject at time t1; measuring the pulmonary artery pressure (PAP2) of the subject at time t2, and calculating PVR according to the equation $PVR = (t2 - t1)/(C \times \ln(PAP1/PAP2))$.

A method for calculating systemic vascular resistance of a subject, without directly measuring wedge pressure, may include the steps of calculating the pulomary vascular resistance of the subject, determining the mean pulmonary artery pressure ($\overline{PAP}$) of the subject; calculating the cardiac output (CO) of the subject; calculating the pulmonary capillary wedge pressure (PCW) according to the equation $PCW = (PVR \times CO)/\overline{PAP}$; determining the mean arterial pressure ($\overline{AOP}$) of the subject; and calculating the systemic vascular resistance of the subject according to the equation $SVR = (\overline{AOP} \times PCW)/CO$.

Alternatively, the systemic vascular resistance (SVR) could be obtained through the equation $SVR = \overline{AOP} \times PVR/\overline{PAP}$. By using this equation, CO and PCW do not have to be obtained or used.

DETAILED DESCRIPTION OF THE ILLUSTRATED EMBODIMENTS

Figure 1:
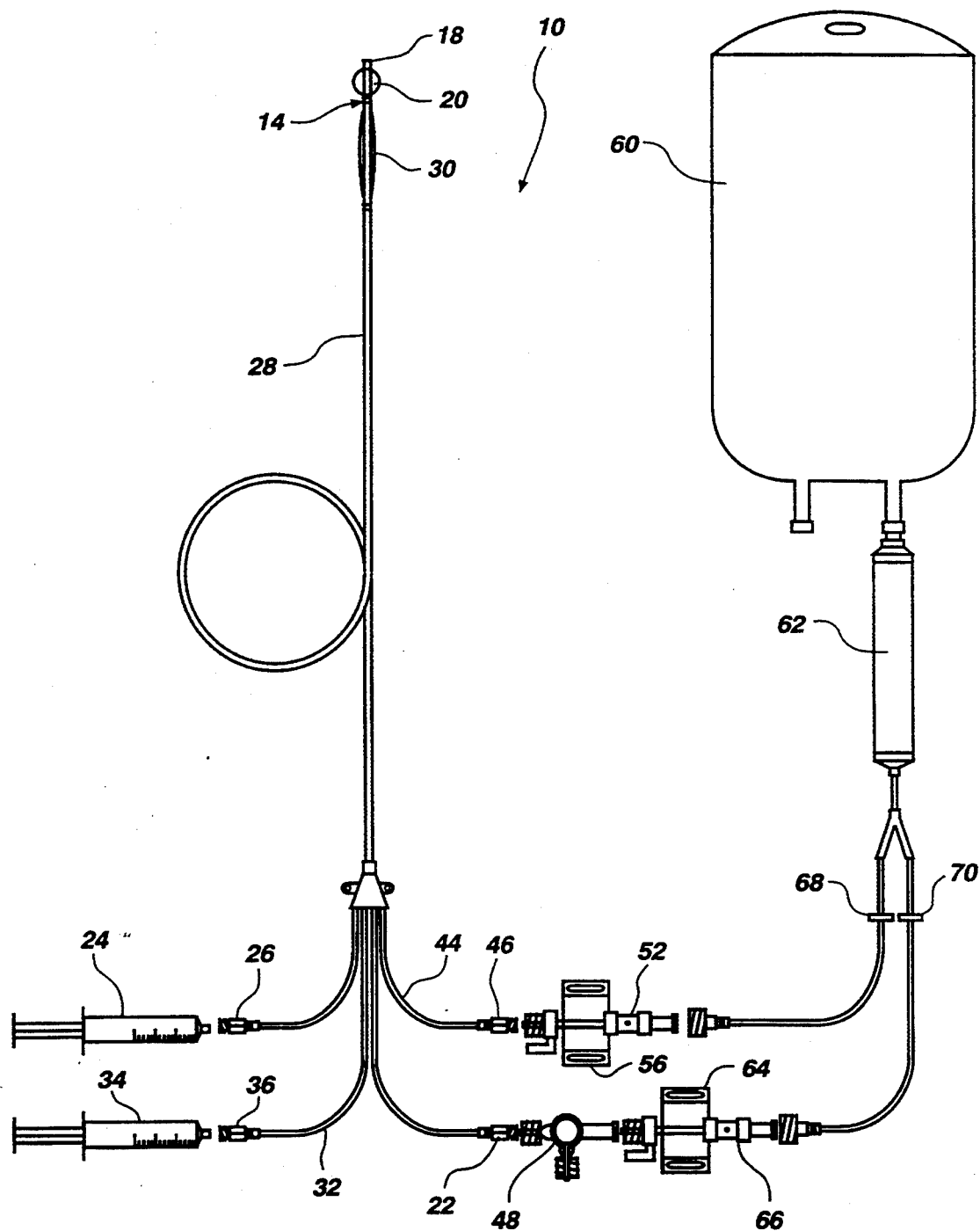
FIG. 1 is schematic representational view of a catheter set according to the present invention.

The present invention includes a method and system for determining vessel compliance by changing the fluid volume within the vessel and noting the resulting Change in pressure.

The invention also includes a method and system for continuously calculating blood flow based on the determined compliance. This method and system is much faster and less invasive than thermal dilution procedures. In addition, it yields more accurate blood flow calculations. The term "blood flow" is used rather than "cardiac output" because the present invention may be used to calculate the rate of flow in various vessels in the body. Cardiac output is merely one example of blood flow.

The invention further includes methods and systems for calculating pulmonary vascular resistance and systemic vascular resistance from pressure versus time measurements for a particular compliance, without measuring wedge pressure.

As used herein, "continuously" does not necessarily mean constantly. As explained above, the compliance of a vessel changes as various factors change. Therefore, the compliance should be regularly (but not necessarily periodically) redetermined as described herein to provide accurate calculation of blood flow. The frequency of redetermination of compliance and blood flow depend on various factors including the administration of drugs. When a computer is employed, the compliance may be redetermined at a frequency of up to more than once a second, although this is far more frequent than expected for most situations. The compliance should be recalculated when the pressure versus time curve changes slope.

The determinations and calculations of the present invention may be made for a subject, whether human or animal.

The determination of vessel compliance is addressed first.

A. Determining Vessel Compliance

In general, the compliance of a vessel may be calculated accordingly to equation (5), below:

$$C = dV/dP \qquad (5),$$

where dV is the change in volume of a vessel and dP is the change in pressure resulting from the change in volume.

Determining the compliance is referred to as calibration because the compliance is a base point used in calculating the blood flow and vascular resistance, described below.

The change in the volume of a vessel may be caused in a variety of ways. For example, the volume may be changed by a rapidly changing the volume of a balloon or rapidly injecting into or removing fluid from the vessel (which may be referred to as a one-shot or bolus method). Alternatively, the volume may be changed through constantly infusing or withdrawing fluid volume by a known amount over a known period of time and comparing the resultant pressure versus time waveform with pressure versus time waveforms over beats before or after the constant change. Blood is relatively incompressible. Therefore, as the balloon expands or contracts or as fluid is added or removed, the vessel expands or contracts by an essentially equal amount. The corresponding change in pressure is measured through standard techniques, such as using a pressure transducer.

FIG. 1 shows a preferred embodiment of a catheter set 10, which is preferably disposable. Catheter set 10 includes a catheter 14 having a distal orifice 18 and a flotation balloon 20, used to drag catheter 14 to the desired location, for example, the pulmonary artery. Catheter 14 may be a standard flow directed thermal dilution catheter, although the present invention does not involve using a thermistor or heating band that may or may not be on the catheter or rapidly injecting cooled or warm fluids. In this respect, catheter set 10 may include more components than are necessary for the invention (including components not shown in FIG. 1), but which may be convenient or desirable for some other purpose. For example, an additional lumen 22 may be desirable for monitoring the central venous pressure, injecting drugs, or performing other procedures through an optional proximal orifice 28 which are not part of the present invention. Catheter set 10 may include the ability to measure wedge pressure, even though measuring wedge pressure might not be used in the present invention. Catheter set 14 could include pacing or ECG sensing leads, fiber optic pulse oximetry channels or additional infusion lumens.

Flotation balloon 20 is inflated by a syringe 24 through a flotation balloon lumen 26. A displacement balloon 30, which may be cigar shaped, is located near flotation balloon 20. A two cubic-centimeter (cc) displacement balloon 30 on a seven french catheter would be approximately two inches (50.8 mm) long and 0.25 inches (6.35 mm) in diameter when inflated. Displacement balloon 30 is positioned "adjacent" to catheter 14, meaning that displacement balloon 30 is touching catheter 14 (preferably near its tip) or is near catheter 14.

Displacement balloon 30 is preferably elastic and conforms closely to shaft of catheter 14 when deflated.

The pressure versus volume curve for balloon 30 should be such that once inflated, the volume remains constant over a wide range of pressures.

To determine the compliance, displacement balloon 30 is inflated during diastole or systole and suddenly deflated during diastole. Displacement balloon 30 is connected to tube 32 and inflated and deflated by means of a syringe 34 connected to a displacement balloon lumen 36.

Alternatively, displacement balloon 30 could be deflated during systole. However, it is believed that deflation during diastole causes a more recognizable change in the pressure versus time waveform. Deflation may be at the end of the exhalation phase of the respiratory cycle. The contraction of the heart during systole adds an unknown volume to the pulmonary artery and complicates the compliance determination. Also, displacement balloon 30 could be suddenly inflated rather than deflated, but it is believed that deflation is faster and easier to control.

Blood pressure may be measured by standard techniques, such as, for example, a pressure transducer 56, which is connected to distal orifice 18 through tube 44 and a distal lumen or connector 46. Saline in a pressure infuser 60 is applied through microdrip unit 62 through a flush set 52 to keep a positive pressure of saline slowly flowing out of distal orifice 18 so that blood does not come into distal orifice 18 and tube 44. Catheter set 10 may include pressure transducer 64 and flush set 66 connected to proximal orifice 28. Stopcock 48 may be used for drug delivery or blood sampling. Infuser 60 may also be connected to flush set 66. Clamps 68 and 70 may be used.

The equation for determining compliance during a normal diastolic interval is shown as equation (6), below:

$$C = dV/dP \tag{6}$$

where dV is the normal change in volume due to diastolic drainage, and dP is the resulting change in pressure. An equation for determining compliance when the volume is changed by a balloon or infusion of fluid is shown as equation (7), below:

$$C = (dV - dV2)/dP2 \tag{7}$$

where dV is the normal change in volume due to diastolic drainage, dV2 is the change in volume created by displacement balloon 30, and dP2 is the resultant change in pressure. Combining equations (6) and (7) yields, equation (8), below:

$$C = dV/dP = (dV - dV2)/dP2 \tag{8}$$

Rearranging terms of equation (8) yields equations (9), (10), (11), and (12), below:

$$dV = C \times dP = (C \times dP2) + dV2 \tag{9}$$

$$(C \times dP) - (C \times dP2) = dV2 \tag{10}$$

$$C(dP - dP2) = dV2 \tag{11}$$

$$C = dV2/(dP - dP2) \tag{12}$$

The value dP represents the difference between a starting pressure and what the pressure would have been at a particular time, but for the deflation of balloon 30. The value dP2 represents the difference between the starting pressure and what the pressure actually is or was at the particular time. Because equation (12) involves the difference between dP and dP2, the starting point is not important, and equation (12) may be rewritten as equation (13), below:

$$C = dV2/(PE - PA) \tag{13}$$

where dV2 is the change in volume of the vessel created by the deflation of displacement balloon 30, PE is an estimate of what the pressure measured by transducer 56 would have been but for the deflation of displacement balloon 30 at a time tx, and PA is the actual pressure measured by transducer 56 at time tx. Time tx is a time at or shortly following the time the pressure versus time curve reaches equilibrium following deflation of displacement balloon 30.

Figure 2:
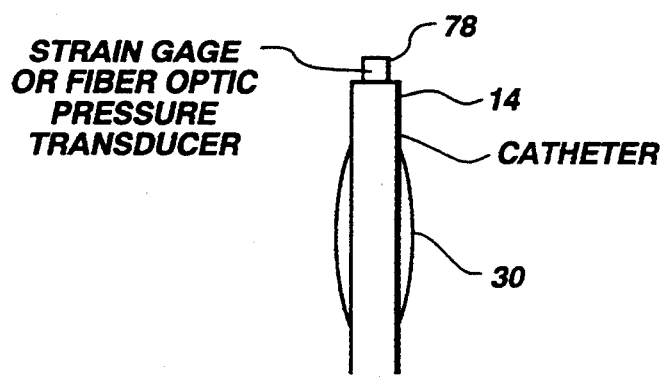
FIG. 2 is a side view of a catheter having a single balloon and a miniaturized strain gage or fiber optic pressure transducer incorporated into the distal tip of the catheter.

Referring to FIG. 2, as opposed to the two balloon arrangement shown in FIG. 1, catheter set 10 may have a single balloon (such as, for example, displacement balloon 30) that acts as both the displacement balloon and the flotation balloon. In that case, the balloon would be inflated to one level when it is to act as a displacement balloon and a second level when it is to act as a flotation balloon. Other options include a employing a displacement balloon 30 but no flotation balloon, which may be particularly useful when the catheter is intended for a location other than the pulmonary artery (e.g., to test the patency of coronary or peripheral vessels). Also, as shown in FIG. 2, a miniaturized strain gage or fiber optic pressure transducer 78 may be incorporated into the distal tip of the catheter (whether one or two balloons are used), replacing the open pressure monitoring lumen for increased signal fidelity and to avoid fluid flush required of open ports.

The orifice that is connected to pressure transducer 56 may be located on the proximal side of displacement balloon 30, rather than on the distal side as is distal orifice 18 in FIG. 1. Likewise, strain gage or fiber optic pressure transducer 78 or other pressure transducer could be located on the proximal side of displacement balloon 30 rather than on the distal side as in FIG. 2.

Figure 3:
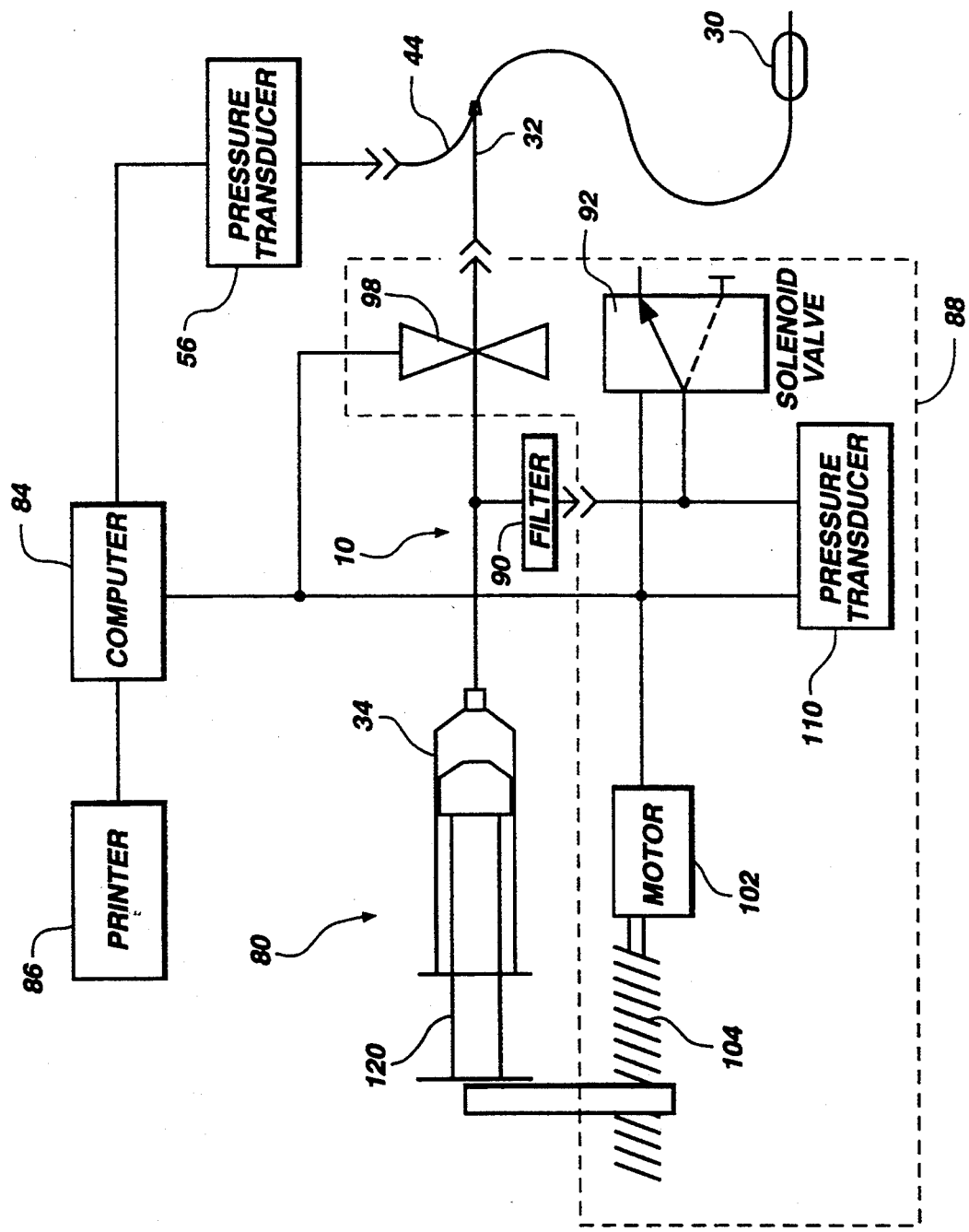
FIG. 3 is a schematic view of a preferred blood flow monitor and calibration system.

FIG. 3 shows a schematic diagram of a preferred blood flow monitor and calibration system 80, which includes processing circuits, such as computer 84. Blood flow monitor and calibration system 80 may also include a printer 86, a syringe position controller 88 (shown in dashed lines), and catheter set 10, only part of which is shown in FIG. 3. Computer 84 controls and monitors components of syringe position controller 88. Computer 84 also monitors pressure transducers 56 and 110, and other pressure transducers, such as pressure transducer 64, as needed. In operation, syringe 34 is preloaded with room air through disposable filter 90 and a solenoid valve 92 connected to the atmosphere. As opposed to using room air, displacement balloon 30 could be inflated through cylinders of compressed gas or by use of a compressor or vacuum pump. There would be a leur type fitting between disposable filter 90 and reusable solenoid valve 92.

Strain gage or fiber optic pressure transducer 78 (shown in FIG. 2) communicates blood pressure information to computer 84 and, therefore, acts as an alternative to pressure transducer 56. Other types of transducers could be used rather than strain gage or fiber optic pressure transducer 78 or pressure transducer 56.

Referring to FIGS. 1 and 3, a solenoid activated pinch clamp 98 on the balloon lumen 36 is closed prior to the time displacement balloon 30 is inflated. To inflate displacement balloon 30, solenoid valve 92 is closed, pinch clamp 98 is opened, and syringe 34 is driven forward by a syringe pump consisting of a motor 102 and a ball screw mechanism 104. Once balloon displacement 30 is inflated to a desired volume, pinch clamp 98 is closed and motor 104 reverses ball screw 104 to create a very low pressure or vacuum in syringe 34 as described below. Computer 84 monitors the pressure at distal orifice 18 of catheter 14 through pressure transducer 56. Computer 84 detects, for example, the peak systolic pressure and releases pinch clamp 98 so that displacement balloon 30 is deflated by a predetermined amount during the diastolic interval. A second pressure transducer 110 connected to syringe 34 is used to monitor the inflation and deflation pressures of syringe 34 and test for any leaks in the system. Computer 84 monitors second pressure transducer 110. Unless otherwise made clear from the context, "pressure" means the blood pressure measured by pressure transducer 56.

It is noted that the functions of blood flow monitor and calibration system 80 could be performed manually. For example, syringe 34 could be operated manually rather than by syringe position controller 88. Solenoid value 92 and pinch clamp 98 could be operated manually. Solenoid value 92 and pinch clamp 98 could be replaced by a stopcock such as stopcock 48 placed between syringe 34 and lumen 36.

In the embodiment in which liquid is injected or withdrawn, an orifice which is similar to orifice 28 and is connected to syringe 34 may be placed near orifice 18, through which pressure is measured. If fluid is injected or withdrawn quickly, a single orifice 18 may be used (unless pressure is measured by a transducer placed in orifice 18). If fluid is injected or withdrawn slowly, two orifices may be required. Pinch clamp 98 may be eliminated. A flush set, similar to flush set 48, is preferably used.

Figure 4:
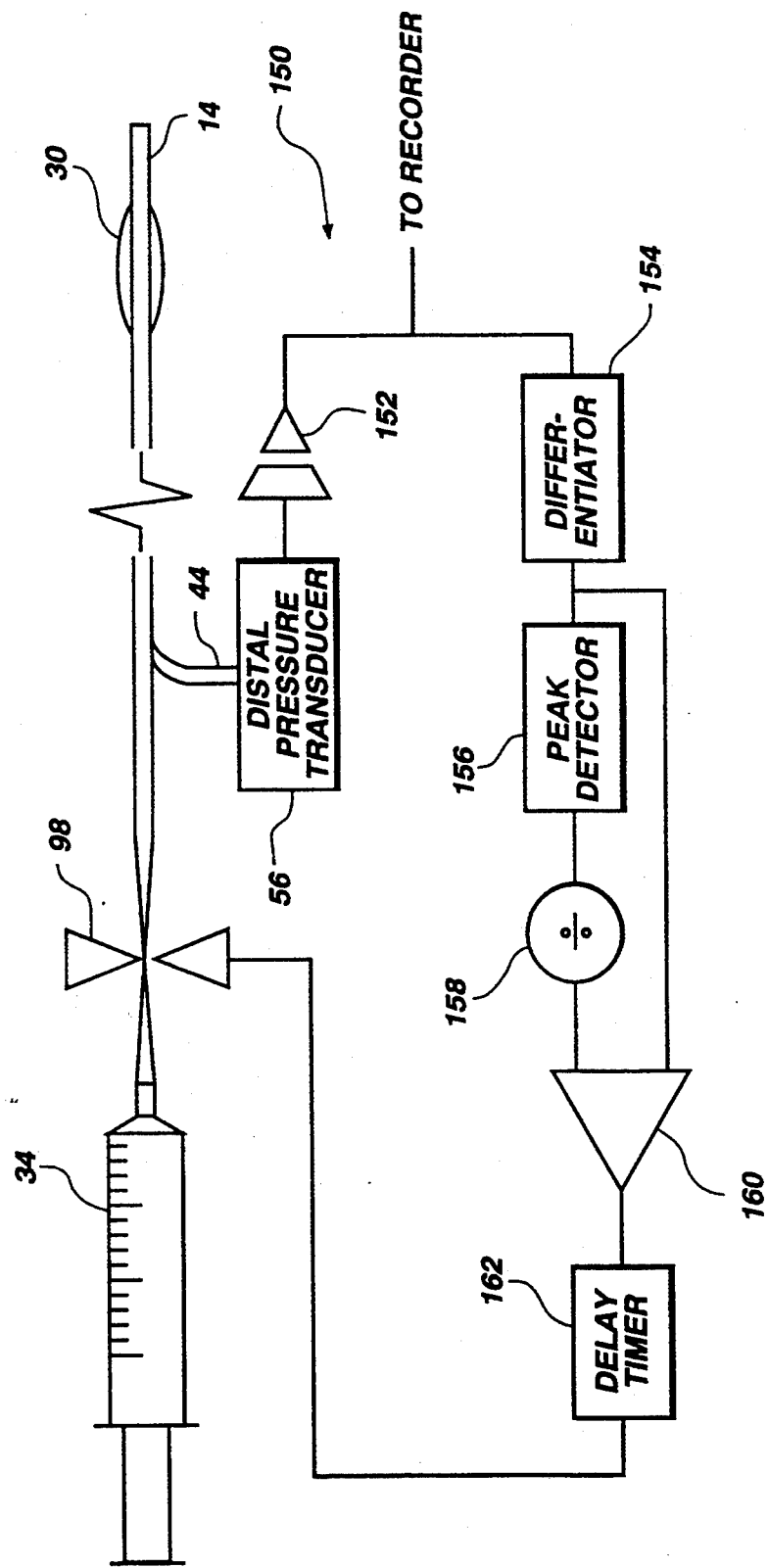
FIG. 4 is a schematic diagram of a circuit to synchronize deflation of the balloon.

FIG. 4 shows a schematic diagram of a circuit 150 that controls clamp 98 synchronously with, for example, the peak systolic pressure. Circuit 150 includes differentiator (or filter) 154 that generates a signal proportional to the slope of the pulmonary artery pressure waveform, a peak detector 156, a divider circuit 158 that reduces the output of peak detector 156 by a fixed amount, and a comparator 160. Comparator 160 generates a trigger signal when the output of differentiator 154 is less than that of peak detector 156. A delay timer 162 opens clamp 98 after a suitable delay from activation of comparator 160. Computer 84 could perform some or all of the functions of circuit 150.

The compliance is determined from equation (12) or equation (13) by a computer or a person through a procedure such as one of the procedures described below. Computer 84 may do all of the calculations required to determine and display compliance. Computer 84 might also display a complete or partially complete cardiac hemodynamic profile including blood flow (e.g., cardiac output), pulmonary vascular resistance, systemic vascular resistance, arterial pressure, and pulmonary artery pressure. Computer 84 could also display flow trending, flow velocity, and system status. Printer 86 may be used to demonstrate trends or provide a permanent record of blood flow and the other parameters.

Figure 5A:
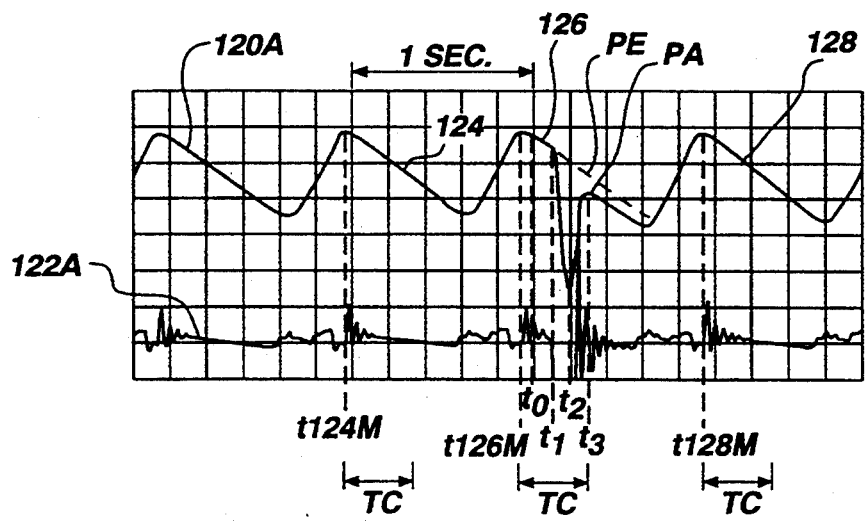
FIG. 5A is a graphical representation of pressure versus time results from a first test.
Figure 5B:
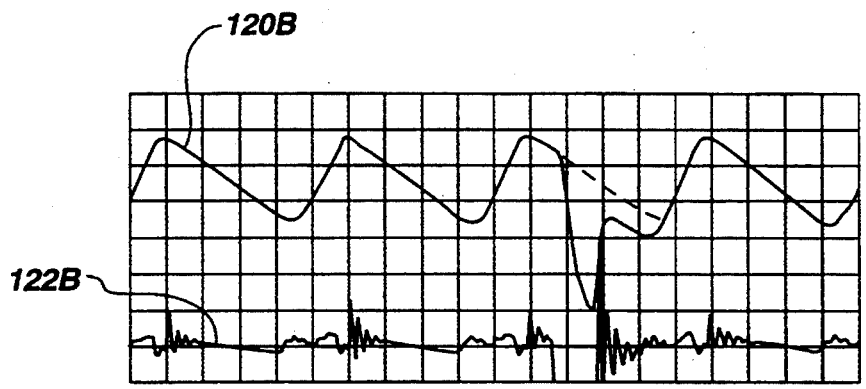
FIG. 5B is a graphical representation of pressure versus time results from a second test.
Figure 5C:
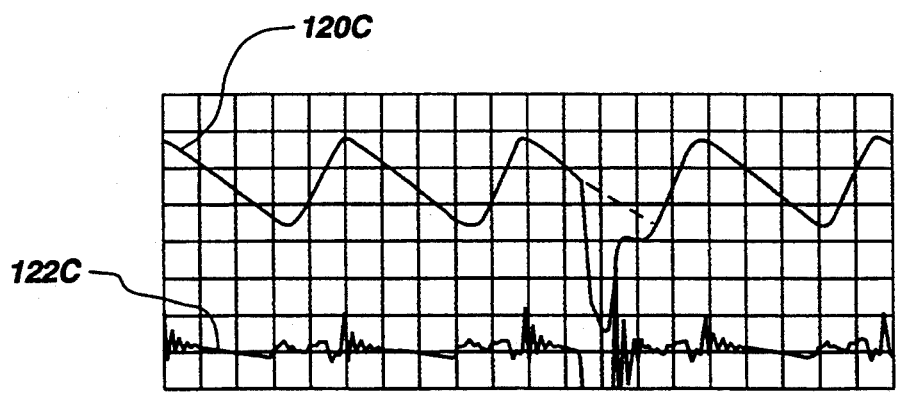
FIG. 5C is a graphical representation of pressure versus time results from a third test.

The procedures are explained in connection with the graphs in FIGS. 5A, 5B, and 5C, which were generated in connection with tests made using a mock circulation with the compliance of the pulmonary artery artificially set so that one cc volume added changed the pressure by one millimeter mercury (mm Hg). Three tests, referred to as test Nos. 1, 2, and 3, are illustrated in FIGS. 5A, 5B, and 5C, respectively. FIGS. 5A, 5B, and 5C include pressure waveforms 120A, 120B, and 120C showing blood pressure versus time, and pressure waveforms 122A, 122B, and 122C showing pressures of syringe 34 versus time.

During diastole, pressure waveforms 120A, 120B, and 120C are essentially linear. In the human heart, by contrast, during diastole, pressure wave 120A is described by the exponentially decaying function in equation (14), below:

$$P(t) = P0 e^{-t/RC} \qquad (14),$$

where P(t) represents the pressure at time t, P0 represents an initial pressure during the main portion of the diastolic interval, R is the lung resistance, and C is the compliance.

Referring to FIG. 5A, at time t0 (which is shortly before time t1), ball screw 104 moves handle 120 of syringe 34 so that the volume of the interior of syringe 34 increases. It is ordinarily desirable that displacement balloon 30 deflate as very quickly (and perhaps as fast as possible). Furthermore, it is preferred that displacement balloon 30 deflate completely. Therefore, in a preferred embodiment, handle 120 is moved so that the volume of the interior of syringe 34 increases by much more than the volume displacement balloon 30 is to later decrease. If displacement balloon 30 is to only deflate by a predetermined amount that is less than its total volume (i.e., some volume remains in displacement balloon 30 after deflation), then the interior of syringe 34 should increase by an amount corresponding to the amount the volume of displacement balloon 30 should later decrease, considering the differing pressures.

Pinch clamp 98 is closed from before time t0 to time t1 so that there is very low pressure in syringe 34. At time t1, pinch clamp 98 is opened so that the volume of displacement balloon 30 rapidly decreases by a known amount, for example, two cc. Graph 122A shows that the pressure of syringe 34 decreases rapidly after time t1. Almost immediately after time t1, as shown in graph 120A, the pressure measured by pressure transducer 56 drops significantly, reaching its lowest point at about time t2 and returning to an equilibrium point at about time t3.

A person can tell where the equilibrium point is by inspection. Computer 84, on the other hand, is programmed to determine the equilibrium point where the pressure curve (represented by graph 120A) starts to decrease (for at least a predetermined time), after sharply increasing. The program could consider ringing or overshoot. The actual pressure after time t3 has a slope that is essentially the same as the slope of the estimated dashed line in FIG. 5A.

The pressure of syringe 34 also raises significantly at about time t3, and eventually settles back to its original state. (The small variations in graph 122A before time t1 and after time t3 are catheter artifact noise.)

The scale of pressure waveforms 120A, 120B, and 120C represents mm Hg. It is interesting to note that in test No. 1 (FIG. 5A), where 2 cc are removed, the difference in pressure dP is about 2 mm Hg. In test No. 2 (FIG. 5B), where 3 cc are removed, the difference in pressure dP is about 3 mm Hg. In test No. 3 (FIG. 5C), where 4 cc are removed, the difference in pressure dP is about 4 mm Hg. There appears to be, therefore, an essentially linear increase in the change in pressure with a change in volume. Similar results were obtained by modifying the compliance and changing the volume by a fixed amount.

In the present example, time tx is time t3, but time tx could be sometime shortly after time t3. Pressures PA and PE are labelled in FIG. 5A. Actual pressure PA is measured by pressure transducer 56.

In practice, deflation of displacement balloon 30 occurs over some finite period of time. This complicates the formula for estimating the estimated pressure PE as there is some additional drainage from the pulmonary artery into the pulmonary bed during this time which is also reflected in the pressure waveform.

A variety of techniques of estimation analysis may be used to estimate estimated pressure PE at time tx, which equals time t3 in the example of FIG. 5A.

A first technique is to extrapolate based on one or more previous diastolic intervals. Pressure waveform 120A includes diastolic intervals 124, 126, and 128. The maximums of pressure waveform 120A is the peak systolic pressure occurring at times t124M, t126M, and t128M, respectively. The length of time between time t126M and time t3 is TC. It is assumed that the pressure waveform does not change much from one diastolic interval to the next diastolic interval. Therefore, the pressure PE at time t3 (which equals time t126M+TC) is assumed to be the same as the actual pressure at time t124M+TC. If the pressure of diastolic interval 124 was not recorded for precisely time t124M+TC, then some interpolation or extrapolation of pressure measurements at about time t124M+TC may have to be made. Also, the pressure PE may be based on averages of more than one previous diastolic interval. (Note that the referencing from the time of the peak systolic pressure as opposed to some other time is merely one way of performing this first technique.)

A second technique is to estimate pressure PE from interpolating between pressure measurement from diastolic intervals before and after interval 126. For example, the PE could be estimated from pressures from times at or about time t124M+TC and time t128M+TC.

A third technique is for a person to visually extrapolate waveform 120A in diastolic interval 126 such as the dashed line in FIG. 5A.

A fourth technique is extrapolation based on equation (14), reproduced below, and actual pressures during diastolic interval 126:

$$P(t) = P0 e^{-t/RC} \quad (14),$$

where P(t) represents the pressure at time t, P0 represents an initial pressure during the main portion of the diastolic interval 126 (e.g., at time t0), R is the lung resistance, and C is the compliance. Dividing both sides of equation (14) by P0; taking the log of both sides of equation (14), and solving for RC yields equation (15), below:

$$RC = t / \ln(P0/P(t)) \quad (15).$$

The value of the product RC can be determined from equation (15) where, for example, P0 is P of curve 120A at time t0 and P(t) is P at time t1.

The value of P(t) on curve 120A at time t3 may then be estimated from equation (14), where RC is calculated from equation (15), and P0 and RC are the same as in equation (15).

To the extent the diastolic interval of curve 120A is characterized by other than equation (14), then other appropriate estimation techniques may be used, which may involve more or less complicated curve fitting or numerical analysis techniques.

In a typical case, balloon 30 comprises only about 4.3% of the cross-sectional area of a vessel and, therefore, does not pose a significant obstruction to flow. Moreover, the pulmonary artery may hold on the order of 100 cc of blood. Nevertheless, the 2 cc withdraw from balloon 30 is significant in the following sense. The 2 cc's are withdrawn from balloon 30 over about 50 msec. During that 50 msec time, about 4 cc pass through a cross-section through which balloon 30 is positioned. 2 cc is 50% of 4 cc, which is a significant amount.

B. Calculating Blood Flow with the Determined Compliance

Having determined compliance C, the blood flow ("BF") may be continuously calculated from equation (16), below:

$$BF = C \times F \, (\overline{Pcd} - \overline{Pab}) (1 + Sa/Da) \quad (16),$$

where, as explained above, F is the heart rate; $\overline{Pcd}$ is the average pressure in the arterial tree at the end of systole; $\overline{Pab}$ is the average pressure in the arterial tree at the end of diastole; Sa is the area under the arterial pressure curve during systolic drainage (shown in FIG. 5-3 of Guyton); and Da is the area under the arterial pressure curve during diastolic drainage (shown in FIG. 5-3 of Guyton). Equation (16) is the same as equation (1) except BF replaces CO.

The values of F, $\overline{Pcd}$, $\overline{Pab}$, Sa, and Da may be determined by computer 84 based on pressures detected by pressure transducer 56.

In a preferred embodiment, the compliance and the blood flow are both automatically calculated by a computer, such as computer 84. The blood flow may be continuously calculated, with the value of the compliance being redetermined only as necessary or desired.

C. Calculating Vascular Resistance

As noted above, pulmonary vascular resistance ("PVR") is the resistance to blood traveling through the lungs to be oxygenated. Systemic vascular resistance ("SVR") is a measure of the resistance of the blood flow in the body other than the lungs. PVR and SVR may be calculated by equations (3) and (4), reproduced below:

$$PVR = (\overline{PAP} \times PCW)/CO \quad (3),$$

$$SVR = (\overline{AOP} \times PCW)/CO \quad (4),$$

where $\overline{PAP}$ is the mean pulmonary artery pressure, $\overline{AOP}$ is mean arterial pressure, PCW is the pulmonary capillary wedge pressure, and CO is the cardiac output.

As explained above, the standard technique for calculating pulmonary and systemic vascular resistances requires measuring wedge pressure.

Figure 6:
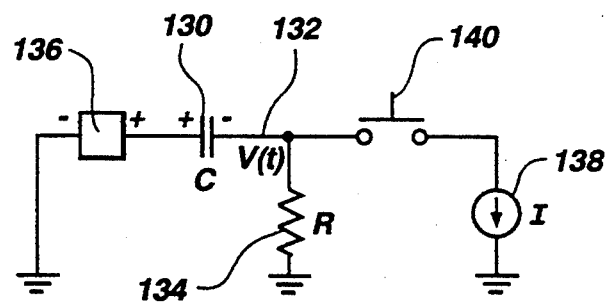
FIG. 6 is a schematic diagram of an electrical circuit that is analogous to pulmonary circulation.

The present invention, by contrast, includes the following methods and systems for calculating PVR and SVR without directly measuring wedge pressures. The methods and systems are illustrated with an electrical analog of the pulmonary circulation shown in FIG. 6. In FIG. 6, a voltage source 136 provides a voltage to one side of a capacitor 130 having capacitance C, the other side of which is connected to a node 132 having a voltage V(t). A resistor 134 having resistance R is connected between node 132 and ground. A current source 138 having a current I is connected between ground and one side of a push button switch 140, the other side of which is connected to node 132.

1. Calculating PVR

In the analogy, voltage is equated with pressure (i.e., PAP), charge is equated with volume, capacitance is equated with compliance, and resistance is equated with vascular resistance (i.e., PVR). The voltage source represents pressure created by the right ventricle of the heart. Removal of current through switch 140 and current source 138 in FIG. 6 represents the decrease in volume of balloon 30. The capacitance (or compliance) of the system is derived from equation (17), below:

$$C = \Delta Q / \Delta V \quad (17),$$

in which $\Delta Q$ is the change in charge (which represents volume) and $\Delta V$ is the change in voltage (which represents pressure).

Figure 7:
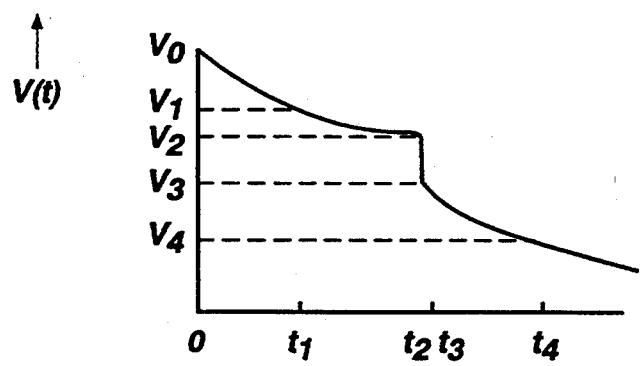
FIG. 7 is a graphical representation of voltage versus time results of the circuit of FIG. 6.

FIG. 7 is a graphical representation of voltage versus time results of the circuit of FIG. 6. The RC time constant may be derived from any two points on continuous segments of the voltage versus time curve (for example, V0 and V1, V0 and V2, V2 and V1, V3 and V4, but not, for example, V0 and V3, V1 and V3, V2 and V3, or V2 and V4). At about time t2, switch 138 is depressed, which represents a decrease in the volume of displacement balloon 30.

As an example, points V1 and V2 are used to determine R. The voltage V(t) at time t is calculated in equation (18), below:

$$V(t) = V0 e^{-t/RC} \quad (18),$$

where V0 is the initial voltage, t is time t, and R and C are defined above. (Note that the times t0–t3 in FIG. 7 are not the same as the times t0–t3 in FIG. 5A.)

At time t1, the voltage is V1, calculated in equation (19), below:

$$V1 = V0 e^{-t1/RC} \quad (19).$$

At time t2, voltage v(t) rapidly decreases from V2 to V3, calculated in equation (20), below:

$$V(t2) = V0 e^{-t2/RC} = V2 \quad (20),$$

which may be rewritten as equation (21), below:

$$V2/V0 = e^{-t2/RC} \quad (21).$$

Taking the log of both sides of equation (21) yields equations (22), below:

$$\ln(V2/V0) = -t2/RC \quad (22).$$

Solving for RC yields equation (23), below:

$$RC = t2/\ln(V0/V2) \quad (23).$$

For times other than zero, equation (18) may be written in equation (24), below:

$$V2 = V0 e^{-t2/RC} = V1 e^{-(t2-t1)/RC} \quad (24).$$

Rewriting equation (24) produces equation (25), below:

$$V2/V1 = e^{-(t2-t1)/RC} \quad (25).$$

Taking the log of both sides of equation (25) yields equation (26), below:

$$\ln(V2/V1) = -(t2-t1)/RC \quad (26).$$

Solving for R yields equation (27), below, which applies for points other than zero:

$$R = (t2-t1)/(C \times \ln(V1/V2)) \quad (27).$$

Equation (27) may be rewritten as equation (28), below:

$$PVR = (t2-t1)/(C \times \ln(PAP1/PAP2)) \quad (28).$$

where R is replaced with PVR, C is the compliance, and PAP1 and PAP2 are the pulmonary artery pressures at times t1 and t2, respectively. The values of PAP1 and PAP2 may be determined by computer 84 based on pressures detected by pressure transducer 56.

Compliance C changes with time. Therefore, the value of the compliance C should be redetermined (for purposes calculating blood flow and PVR and SVR) as necessary. The value of the compliance C should be redetermined when the slope of the pressure versus time curve changes or when the blood velocity changes. Also, it is possible for the slope of the pressure versus time curve to remain constant because the product of R and C remains constant although the individual values of R and C have changed. Therefore, the value of the compliance C should be occasionally redetermined even if the slope remains constant.

2. Calculating SVR

As noted above, systemic vascular resistance SVR may be calculated from equation (4), reproduced below:

$$SVR = (\overline{AOP} \times PCW)/CO \quad (4),$$

where $\overline{AOP}$ is mean arterial pressure, PCW is the pulmonary capillary wedge pressure, and CO is the cardiac output. $\overline{AOP}$ may be measured through well known techniques through an auxilary catheter and pressure transducer in an artery, similar to catheter set 10 and computer 84. CO may be measured as described above or through some other technique.

The value of PCW (for equation (4)) may be calculated noninvasively as follows. Solving for PCW in equation (3), above, produces equation (29), below:

$$PCW = (PVR \cdot CO)/\overline{PAP} \quad (29).$$

The value of PVR is calculated from equation (28). $\overline{PAP}$ may be measured by well known techniques through an pressure transducer 56 and computer 84. The calculated value of PCW in equation (29), $\overline{AOP}$, and CO are then inserted into equation (4).

Alternatively, SVR may be calculated from equation (30), below, which is derived from equation (29) inserted into equation (4):

$$SVR = (\overline{AOP} \times ((PVR \times CO)/\overline{PAP})/CO \quad (30)$$
$$= \overline{AOP} \times PVR/\overline{PAP}.$$

By using equation (30), CO does not have to be measured or used and PCW does not have to be calculated or used.

The pressure versus time measurements for PVR and SVR calculations are preferably made during the diastolic interval of the cardiac cycle. PVR and SVR may be calculated by a computer, such as computer 84, or by inspection, by developing a compliance curve for difference pressure changes, similar to that shown in FIG. 7.

The system for calculating pulmonary vascular resistance is the same as that described in connection with FIGS. 1 and 3. The system for systemic vascular resistance is the same as that described in connection with FIGS. 1 and 3, except that arterial pressure is also measured by an arterial catheter and another pressure transducer, and a monitor, or a pressure cuff.

D. Blood Velocity

The computer may also calculate and display the instantaneous velocity of flow. Instantaneous velocity has been equated to the dP/dT of the pressure waveform. (See Jones, et al, "Velocity of blood flow and stroke volume obtained from the pressure pulse," *J. Clin Invest*, 38:2087-2090, 1959.).

The instantaneous change in pressure per change in time (dP/dt) is related to velocity as shown in equation (31), below:

$$-dP/dx = \rho dv/dt + fv \quad (31),$$

where v is the instantaneous blood velocity, x is the axial coordinate of the vessel, t is time, $\rho$ is blood density, and f is a blood friction constant.

The change in pressure per change in axial coordinate of the vessel may also be written as in equation (32), below:

$$-dP/dx = 1/S \, dP/dt \quad (32),$$

where S is the pressure pulse wave velocity in the vessel.

Substituting equation (32) into equation (31) yields equation (33), below:

$$dP/dt = \rho S \, dv/dt + Sfv \quad (33).$$

Those having skill in the art will appreciate that many changes may be made to the details of the above-described methods and systems without departing from the underlying principles of the invention. Accordingly, the scope of the present invention should be determined only by the following claims.

What is claimed is:

1. A system for determining compliance of a vessel, the system comprising:
   a displacement balloon insertable into the vessel;
   a tube having at least first and second openings, the first opening being connected to the displacement balloon;
   an adjustable pressure source connected to the second opening of the tube that selectively changes volume of the displacement balloon by an amount, thereby changing volume of the vessel by essentially the amount;
   pressure detecting means for measuring blood pressure in the vessel at a position near the displacement balloon and generating a pressure signal indicative of the measured blood pressure; and
   processing means for receiving the pressure signal, determining change in blood pressure caused by the change in volume of the displacement balloon, and determining the compliance based on the change in volume and the change in blood pressure.

2. The system of claim 1 in which compliance C is determined according to an equation C = dV2 / (PE−PA), where C is the compliance, dV2 is the change in volume created by the displacement balloon, PE is an estimate of what the blood pressure would have been but for the change in volume of the displacement balloon at a particular timer and PA is the actual blood pressure at the particular time.

3. The system of claim 1 in which the displacement balloon is positioned adjacent a catheter and in which the pressure detecting means is a miniaturized strain gage placed adjacent to the catheter.

4. The system of claim 1 in which the displacement balloon is positioned adjacent a catheter and in which the pressure detecting means is a fibre optic pressure transducer placed adjacent to the catheter.

5. The system of claim 1 in which the processing means detects peak systole and the processing means controls the adjustable pressure source in response to the detection of peak systole.

6. The system of claim 1 further comprising a second tube with a first opening near the displacement balloon and a second opening connected to the pressure detecting means.

7. The system of claim 1 in which in the function of determining of the change in blood pressure caused by the change in volume of the displacement balloon performed by the processing means includes estimating what the blood pressure would have been at a particular time but for the change in the volume of the displacement balloon.

8. The system of claim 1 in which the change in volume is a decrease in volume of the displacement balloon.

9. The system of claim 1 in which the vessel is the pulmonary artery.

10. The system of claim 1 in which the displacement balloon also acts as a floatation balloon.

11. The system of claim 1 in which the processing means calculates blood flow through an equation that includes the determined compliance.

12. The system of claim 11 in which all variables of in the equation are derived from the pressure detecting means.

13. The system of claim 1 in which the processing means calculates pulmonary vascular resistance through an equation that includes the determined compliance.

14. The system of claim 13 in which all variables of in the equation are derived from the pressure detecting means.

15. The system of claim 1 in which the processing means calculates systemic vascular resistance through an equation that includes the determined compliance.

16. A system for determining compliance of a vessel, the system comprising:

a catheter that is insertable into the vessel;

a tube having at least first and second openings, the first opening being positioned in the vessel;

an adjustable pressure source that holds fluid and that is connected to the second opening of the tube, the adjustable pressure source selectively changes volume of fluid in the adjustable pressure source by a predetermined amount, thereby changing volume of the vessel by essentially the predetermined amount;

pressure detecting means for measuring blood pressure in the vessel and generating a pressure signal indicative of the measured blood pressure; and processing means for receiving the pressure signal, determining change in blood pressure caused by the change in volume of the fluid, and determining the compliance through an equation that includes the change in volume and the change in blood pressure.

17. The system of claim 16 in which the adjustable pressure source changes the volume of fluid in the adjustable pressure source by injecting fluid into the vessel.

18. The system of claim 16 in which the adjustable pressure source changes the volume of fluid in the adjustable pressure source by withdrawing fluid from the vessel.

19. A method for determining compliance of a vessel, the method comprising the steps of:

inserting a displacement balloon into the vessel, the displacement balloon being connected to a first opening of a tube having at least first and second openings, the second end being connected to an adjustable pressure source;

changing the pressure of the adjustable pressure source so as to change volume of the displacement balloon by a predetermined amount;

sensing blood pressure in the vessel at a position near the displacement balloon;

determining change in blood pressure caused by the change in volume of the displacement balloon, and determining the compliance through an equation that includes the change in volume and the change in blood pressure.

20. A method for calculating blood flow in a vessel, the method comprising:

determining the compliance of the vessel by determining a change in pressure caused by a change in volume in the vessel; and calculating the blood flow according to an equation in which the compliance is a parameter.

21. A system for calculating blood flow of blood in a vessel of a subject, comprising:

a displacement balloon that is insertable into the vessel;

a tube having at least first and second openings, the first opening being connected to the displacement balloon;

an adjustable pressure source connected to the second opening of the tube that selectively changes volume of the displacement balloon by an amount, thereby changing the volume of the vessel by essentially the amount;

pressure detecting means for measuring blood pressure in the vessel at a position near the displacement balloon and generating a pressure signal indicative of the measured blood pressure;

processing means for receiving the pressure signal, determining change in blood pressure caused by the change in volume of the displacement balloons and determining the compliance based on an equation that includes the change in volume and the change in blood pressure;

the processing means using the pressure signal for measuring heart rate (F) of the subject, for measuring an average pressure ($\overline{Pcd}$) in the arterial tree of the subject at end of systole, measuring an average pressure ($\overline{Pab}$) in the arterial tree of the subject at end of diastole, generating an arterial pressure curve of the subject during systolic drainage and an arterial pressure curve of the subject during diastolic drainage, measuring area (Sa) under the arterial pressure curve during systolic drainage, measuring area (Da) under the arterial pressure curve during diastolic drainage, and calculating BF according to an equation BF=C×F ($\overline{Pcd}-\overline{Pab}$) (1+Sa/Da).

22. A method for calculating pulmonary vascular resistance (PVR) of a subject, without directly measuring pulmonary capillary wedge pressure, the method comprising the steps of:

determining the compliance C of pulmonary artery of the subject through a procedure that includes measuring blood pressure;

measuring pulmonary artery pressure (PAP1) of the subject at time t1;

measuring pulmonary artery pressure (PAP2) of the subject at time t2; and calculating PVR according to an equation PVR=(t2−t1)/(C×ln(PAP1/PAP2)).

23. The method of claim 22 in which the procedure for determining C comprises the steps of:

inserting a displacement balloon into the vessel, the displacement balloon being connected to a first opening of a tube having at least first and second openings, the second being connected to an adjustable pressure source;

changing the pressure of the adjustable pressure source so as to change volume of the displacement balloon by a predetermined amount;

sensing blood pressure in the vessel at a position near the displacement balloon;

determining change in blood pressure caused by the change in volume of the displacement balloon, and determining the compliance through an equation that includes the change in volume and the change in blood pressure.

24. A method for calculating systemic vascular resistance (SVR) of a subject, without directly measuring pulmonary capillary wedge pressure, the method comprising the steps of:

calculating pulmonary vascular resistance (PVR) of the subject;

determining mean pulmonary artery pressure ($\overline{PAP}$) of the subject;

calculating cardiac output (CO) of the subject;

determining mean arterial pressure ($\overline{AOP}$) of the subject;

calculating the pulmonary capillary wedge pressure (PCW) according to an equation PCW=(PVR×CO)/$\overline{PAP}$; and calculating the systemic vascular resistance of the subject according to an equation SVR=($\overline{AOP}$×PCW)/CO; and in which the PVR is calculated according to a method including the determining compliance of the subject through a procedure that includes measuring blood pressure;

measuring pulmonary artery pressure (PAP1) of the subject at time t1;

measuring pulmonary artery pressure (PAP2) of the subject at time t2; and calculating PVR according to an equation PVR=(t2−t1)/(C×ln(PAP1/PAP2)).

25. A method for calculating systemic vascular resistance (SVR) of a subject, the method comprising the steps of:

calculating pulmonary vascular resistance (PVR) of the subject;

determining mean arterial pressure ($\overline{AOP}$) of the subject;

determining mean pulmonary artery pressure ($\overline{PAP}$) of the subject;

calculating the SVR of the subject according to an equation SVR=$\overline{AOP}$×PVR/$\overline{PAP}$; and in which the PVR is calculated according to a method including the steps of:

determining compliance of the subject through a procedure that includes measuring blood pressure;

measuring pulmonary artery pressure (PAP1) of the subject at time t1;

measuring pulmonary artery pressure (PAP2) of the subject at time t2; and calculating PVR according to an equation PVR=(t2−t1)/(C×ln(PAP1/PAP2)).

26. A system for determining compliance of a vessel, the system comprising:

a catheter that is insertable into the vessel;

a displacement balloon positioned adjacent to the catheter;

a tube having at least first and second openings, the first opening being connected to the displacement balloon;

an adjustable pressure source connected to the second opening of the tube that selectively changes volume of the displacement balloon by a predetermined amount, thereby changing volume of the vessel by essentially the predetermined amount;

pressure detecting means for measuring blood pressure in the vessel at a position near the displacement balloon and generating a pressure signal indicative of the measured blood pressure; and processing means for receiving the pressure signal, determining change in blood pressure caused by the change in volume of the displacement balloon, and determining the compliance based on the change in volume and the change in blood pressure.

* * * * *

UNITED STATES PATENT AND TRADEMARK OFFICE
CERTIFICATE OF CORRECTION

PATENT NO. : 5,423,323

DATED : June 13, 1995

INVENTOR(S) : Jeffrey L. Orth

It is certified that error appears in the above-indentified patent and that said Letters Patent is hereby corrected as shown below:

In the Abstract, line 17, after "may" insert --be--;

In Column 2, line 9, delete "the during";

In Column 2, line 18, change "Pcd" to --$\overline{Pcd}$--;

In Column 2, line 19, change "Pab" to --$\overline{Pab}$--;

In Column 3, line 53, after "may" insert --be--;

In Column 4, line 51, change "determine" to --determining--;

In Column 4, line 61, change "pulomary" to --pulmonary--;

In Column 5, line 36 change "Change" to --change--;

In Column 6, line 54, change "14" to --10--;

In Column 9, line 9, change "104" to --102--;

In Column 9, lines 28 and 29, change "value" to --valve--;

In Column 9, line 40, change "flush set 48" to --stopcock 48--;

In Column 10, line 29, after "deflate" delete "as";

In Column 12, line 17, change "withdraw" to --withdrawn--;

In Column 13, line 36, change "138" to --140--;

In Column 14, line 59, in the equation, change "PVR'" to --PVR X--;

UNITED STATES PATENT AND TRADEMARK OFFICE
CERTIFICATE OF CORRECTION

PATENT NO. : 5,423,323

DATED : June 13, 1995

INVENTOR(S) : Jeffrey L. Orth

It is certified that error appears in the above-indentified patent and that said Letters Patent is hereby corrected as shown below:

In Column 15, line 8, change the comma to a period;

In Column 16, line 19, change "timer" to --time,--;

In Column 18, line 3, change "balloons" to --balloon,--; and

In Column 19, line 2, after "the" insert --steps of:--.

Signed and Sealed this

Twenty-eighth Day of May, 1996

Attest:

BRUCE LEHMAN

*Attesting Officer*    *Commissioner of Patents and Trademarks*